US010675112B2

(12) United States Patent
Baril et al.

(10) Patent No.: US 10,675,112 B2
(45) Date of Patent: Jun. 9, 2020

(54) ENDOSCOPIC SURGICAL CLIP APPLIER INCLUDING COUNTER ASSEMBLY

(71) Applicant: Covidien LP, Mansfield, MA (US)

(72) Inventors: Jacob C. Baril, Norwalk, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 174 days.

(21) Appl. No.: 16/012,884

(22) Filed: Jun. 20, 2018

(65) Prior Publication Data

US 2019/0038375 A1 Feb. 7, 2019

Related U.S. Application Data

(60) Provisional application No. 62/541,873, filed on Aug. 7, 2017.

(51) Int. Cl.
*A61B 90/00* (2016.01)
*A61B 17/128* (2006.01)
*A61B 17/00* (2006.01)

(52) U.S. Cl.
CPC .......... *A61B 90/08* (2016.02); *A61B 17/1285* (2013.01); *A61B 2017/00367* (2013.01); *A61B 2090/0803* (2016.02)

(58) Field of Classification Search
CPC .............. A61B 17/128; A61B 17/1222; A61B 17/1285; A61B 2019/4815; A61B 90/08; A61B 2090/0803; A61B 2017/00367
See application file for complete search history.

(56) References Cited

U.S. PATENT DOCUMENTS 3,120,230 A 2/1964 Skold
3,363,628 A 1/1968 Wood
(Continued)

FOREIGN PATENT DOCUMENTS

AU 2013254887 A1 11/2013
CA 1163889 A 3/1984
(Continued)

OTHER PUBLICATIONS

The extended European Search Report corresponding to European Application No. EP 07 25 3905.9, completed Jan. 29, 2008; dated Feb. 7, 2008; (7 Pages).
(Continued)

*Primary Examiner* — Tan-Uyen T Ho
*Assistant Examiner* — Lee O Chedister

(57) ABSTRACT

A surgical clip applier includes a counter assembly including a counting wheel with a plurality of actuation features, a locking spring assembly, a driver, and a pin assembly. The counting wheel includes indicia visible through the handle assembly. The locking spring assembly is positioned within the counting wheel and is configured to prohibit multidirectional rotation of the counting wheel. The driver includes a grasping protrusion and a positioning protrusion. The driver translates between a proximal position and a distal position, wherein the grasping protrusion engages the plurality of actuation features to rotate the counting wheel to change the indicia. The pin assembly is configured to engage with the positioning protrusion of the driver, wherein during transitioning of the driver from the proximal position to the distal position, the positioning protrusion engages the stationary pin to pivot the driver, whereby the driver disengages from the plurality of actuation features.

19 Claims, 7 Drawing Sheets

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |

(56) References Cited

U.S. PATENT DOCUMENTS

| | | |
|---|---|---|
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |

(56) References Cited

U.S. PATENT DOCUMENTS

| | | |
|---|---|---|
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |

(56) References Cited

U.S. PATENT DOCUMENTS

| | | |
|---|---|---|
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |

(56) References Cited

U.S. PATENT DOCUMENTS

| | | |
|---|---|---|
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079913 A1* | 4/2006 | Whitfield ............ A61B 17/0682 606/142 |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0235440 A1* | 10/2006 | Huitema ................ A61B 17/10 606/142 |
| 2006/0235441 A1* | 10/2006 | Huitema ................ A61B 17/12 606/142 |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0093856 A1* | 4/2007 | Whitfield ............ A61B 17/1285 606/142 |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |

(56) References Cited

U.S. PATENT DOCUMENTS

| | | |
|---|---|---|
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0137323 A1* | 6/2011 | Malkowski .......... A61B 17/068 606/143 |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1* | 5/2013 | Hartoumbekis ... A61B 17/1285 606/143 |
| 2013/0165951 A1 | 6/2013 | Blake, III |
| 2013/0172909 A1 | 7/2013 | Harris |
| 2013/0172910 A1 | 7/2013 | Malkowski |
| 2013/0172911 A1* | 7/2013 | Rockrohr ............. A61B 17/064 606/143 |
| 2013/0175320 A1 | 7/2013 | Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0209670 A1* | 7/2014 | Thornton ............. G06M 1/083 235/103 |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0046208 A1* | 2/2019 | Baril .................. A61B 34/35 |
| 2019/0053808 A1* | 2/2019 | Baril ................ A61B 17/1285 |

FOREIGN PATENT DOCUMENTS

| | | | |
|---|---|---|---|
| CN | 104605911 B | 2/2017 | |
| DE | 202005001664 U1 | 5/2005 | |
| DE | 202007003398 U1 | 6/2007 | |
| DE | 202009006113 U1 | 7/2009 | |
| EP | 0000756 A1 | 2/1979 | |
| EP | 0406724 A1 | 1/1991 | |
| EP | 0514139 A2 | 11/1992 | |
| EP | 0732078 A2 | 9/1996 | |
| EP | 1712189 A2 * | 10/2006 | ............ A61B 17/10 |
| EP | 1769757 A1 | 4/2007 | |
| EP | 2332471 A1 * | 6/2011 | .......... A61B 17/128 |
| GB | 2073022 A | 10/1981 | |
| JP | 2003033361 A | 2/2003 | |
| JP | 2006154230 A | 6/2006 | |
| JP | 2006277221 A | 10/2006 | |
| JP | 2008017876 A | 1/2008 | |
| WO | 0042922 A1 | 7/2000 | |
| WO | 0166001 A2 | 9/2001 | |
| WO | 0167965 A1 | 9/2001 | |
| WO | 2016192096 A1 | 12/2016 | |
| WO | 2016192718 A2 | 12/2016 | |
| WO | 2016197350 A1 | 12/2016 | |
| WO | 2016206015 A1 | 12/2016 | |

OTHER PUBLICATIONS

International Search Report corresponding to International Application No. PCT-US08-58185, completed Sep. 4, 2008; dated Sep. 9, 2008; (2 Pages).

The International Search Report corresponding to International Application No. PCT-US08-59859, completed Sep. 14, 2008; dated Sep. 18, 2008; (2 Pages).

The extended European Search Report corresponding to European Application No. EP 07 25 3807.7, completed Nov. 7, 2008; dated Nov. 26, 2008; (11 Pages).

The extended European Search Report corresponding to European Application No. EP 09 25 2049.3, completed Dec. 11, 2009; dated Jan. 12, 2010; (3 Pages).

The extended European Search Report corresponding to European Application No. EP 09 25 2050.1, completed Dec. 23, 2009; dated Jan. 21, 2010; (3 Pages).

(56) References Cited

OTHER PUBLICATIONS

The extended European Search Report corresponding to European Application No. EP 09 25 2051.9, completed Dec. 21, 2009; dated Jan. 28, 2010; (3 Pages).
The extended European Search Report corresponding to European Application No. Ep 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).

The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
International Search Report and Written Opinion corresponding to counterpart Int'l Appln. No. PCT/US2018/045306 dated Jan. 16, 2019.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.

(56) References Cited

OTHER PUBLICATIONS

Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 34475 dated Apr. 4, 2017.
Chinese First Office Action corresponding to Chinese Appln. No. CN 2014100088775 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.

* cited by examiner

ENDOSCOPIC SURGICAL CLIP APPLIER INCLUDING COUNTER ASSEMBLY

CROSS-REFERENCE TO RELATED APPLICATIONS

This application claims the benefit of and priority to U.S. Provisional Patent Application No. 62/541,873 filed Aug. 7, 2017, the entire disclosure of which is incorporated by reference herein.

BACKGROUND

Technical Field

The presented disclosure relates generally to surgical clip appliers. More particularly, the present disclosure relates to an endoscopic surgical clip applier having a counter assembly.

Discussion of Related Art

Surgical clip appliers offer surgeons an alternative to conventional suturing of body tissues and vessels. Surgical clip appliers generally store a plurality of clips which are fed sequentially to a jaw mechanism at the distal end of the instrument upon opening and closing of handles at the proximal end of the instrument. As the handles are closed, the jaw members close to deform a clip positioned between the jaw members, and as the jaw members are opened to release the deformed clip, a new clip is fed from the plurality of clips to a position between the jaw members. This process is repeated until all the clips in the plurality of clips have been used.

A need exists for a user of the clip applier to know how many clips remain in the clip applier and/or to know when a final clip of the plurality of clips has been fired.

SUMMARY

The presented disclosure relates to endoscopic surgical clip appliers having a counter assembly. The surgical clip applier includes a handle assembly, an elongated member, a rack bar, and a counter assembly. The elongated member extends distally from the handle assembly. The rack bar is translatably supported in the handle assembly. The counter assembly is supported in the handle assembly and includes a housing, a stationary post, a counting wheel, a locking spring assembly, a driver, and a pin assembly. The housing includes a first housing half and a second housing half. The stationary post is positioned within the first housing half and includes a plurality of locking teeth. The counting wheel is positioned to rotate within the housing, and includes indicia visible through the handle assembly. A plurality of actuation features are positioned circumferentially about the counting wheel. The locking spring assembly includes a plurality of fingers, is positioned within the counting wheel, and is configured to engage the plurality of locking teeth of the stationary post. The engagement of the plurality of fingers of the locking spring assembly and the plurality of locking teeth of the stationary post prohibits multidirectional rotation of the counting wheel. The driver is coupled to the rack bar for translation therewith.

The driver includes a grasping protrusion and a positioning protrusion. The driver is positioned to translate between a proximal position and a distal position. The transitioning of the driver from the proximal position to the distal position causes the grasping protrusion of the driver to engage an actuation feature of the plurality of actuation features to rotate the counting wheel to change the indicia of the counting wheel visible through the handle assembly. The pin assembly includes a stationary pin configured to engage with the positioning protrusion of the driver. During transition of the driver from the proximal position to the distal position, the positioning protrusion of the driver engages the stationary pin to pivot the driver, whereby the driver disengages from the plurality of actuation features of the counting wheel.

In some embodiments, the pin assembly further includes a vertical translating pin, a horizontal translating pin, and a spring. Each of the vertical translating pin, horizontal translating pin, and spring may be configured to permit the engagement and the disengagement between the stationary pin of the pin assembly and the positioning protrusion of the driver. The spring may be connected to the vertical translating pin thereby allowing the vertical translating pin to transition between a first position and a second position. The driver may define a channel configured to receive the vertical translating pin of the pin assembly thereby connecting the driver to the pin assembly. The vertical translating pin may be positioned within a vertical slot defined in at least one of the first housing half or the second housing half. The vertical translating pin may be biased to the first position by the spring. The vertical translating pin may translate between the first and second position in response to the driver engaging with the positioning protrusion.

In embodiments, the surgical clip applier further includes an actuator coupled to the rack bar and the driver. The horizontal translating pin may couple the driver to the actuator. The horizontal translating pin may translate in response to a translation of the actuator and thereby causing the driver to translate. The actuator may be positioned within an actuator slot defined in at least one of the first housing half and second housing half. The actuator may translate in response to the translation of the rack bar and the driver translates in response to the translation of the actuator. In embodiments, the first housing half defines a linear channel configured to receive the driver.

In embodiments, each finger of the plurality of fingers of the locking spring assembly is resilient and flexible, and extends in a substantially tangential direction to an inner surface of the counting wheel. The substantially tangential orientation and length of each finger of the plurality of fingers may prohibit multidirectional rotation of the counting wheel. In other embodiments, the locking spring assembly includes a plurality of bodies and a plurality of fingers. The plurality of fingers may extend from the plurality of bodies.

In other embodiments, the housing further defines a circular recess configured to receive the counting wheel. The stationary post may be concentrically positioned within the first housing half in relation to the circular recess. The second housing half may define an aperture configured to receive the counting wheel.

The surgical clip applier may further include a plurality of surgical clips disposed within the elongated member. The indicia of the counting wheel may indicate a remaining number of the plurality of surgical clips. A number of actuation features of the plurality of actuation features may be equal to an initial number of surgical clips of the plurality of surgical clips. In some embodiment, the indicia may include a plurality of numbers to indicate the remaining number of surgical clips of the plurality of surgical clips. In other embodiments, the indicia include color to indicate the remaining number of surgical clips of the plurality of surgical clips.

Other aspects, features, and advantages will be apparent from the description, the drawings, and the claims that follow.

BRIEF DESCRIPTION OF THE DRAWINGS

An illustrative embodiment of a surgical clip applier with a counter assembly is disclosed herein with reference to the drawings wherein.

DETAILED DESCRIPTION OF EMBODIMENTS

Figures 1A, 1B:
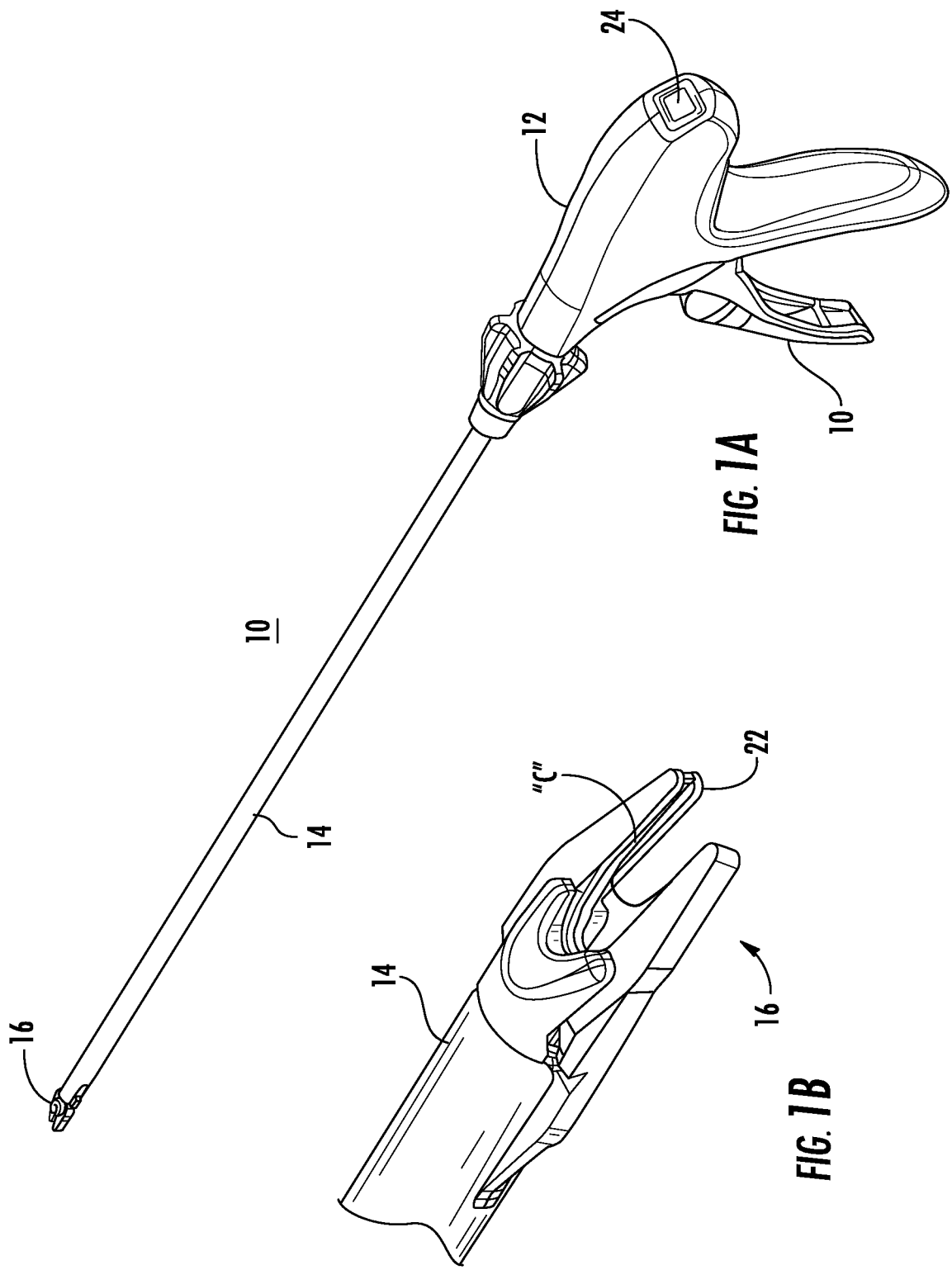
FIG. 1A is a perspective view of a surgical clip applier according to the present disclosure.
FIG. 1B is an enlarged perspective view of a jaw structure of the surgical clip applier of FIG. 1A.

Embodiments of surgical clip appliers in accordance with the present disclosure will now be described in detail with reference to the drawings wherein like reference numerals identify similar or identical structural elements. As shown in the drawings and described throughout the following description, as is traditional when referring to relative positioning on a surgical instrument, the term "proximal" refers to the end of the apparatus which is closer to a user and the term "distal" refers to the end of the apparatus which is farther away from the user.

Figure 2:
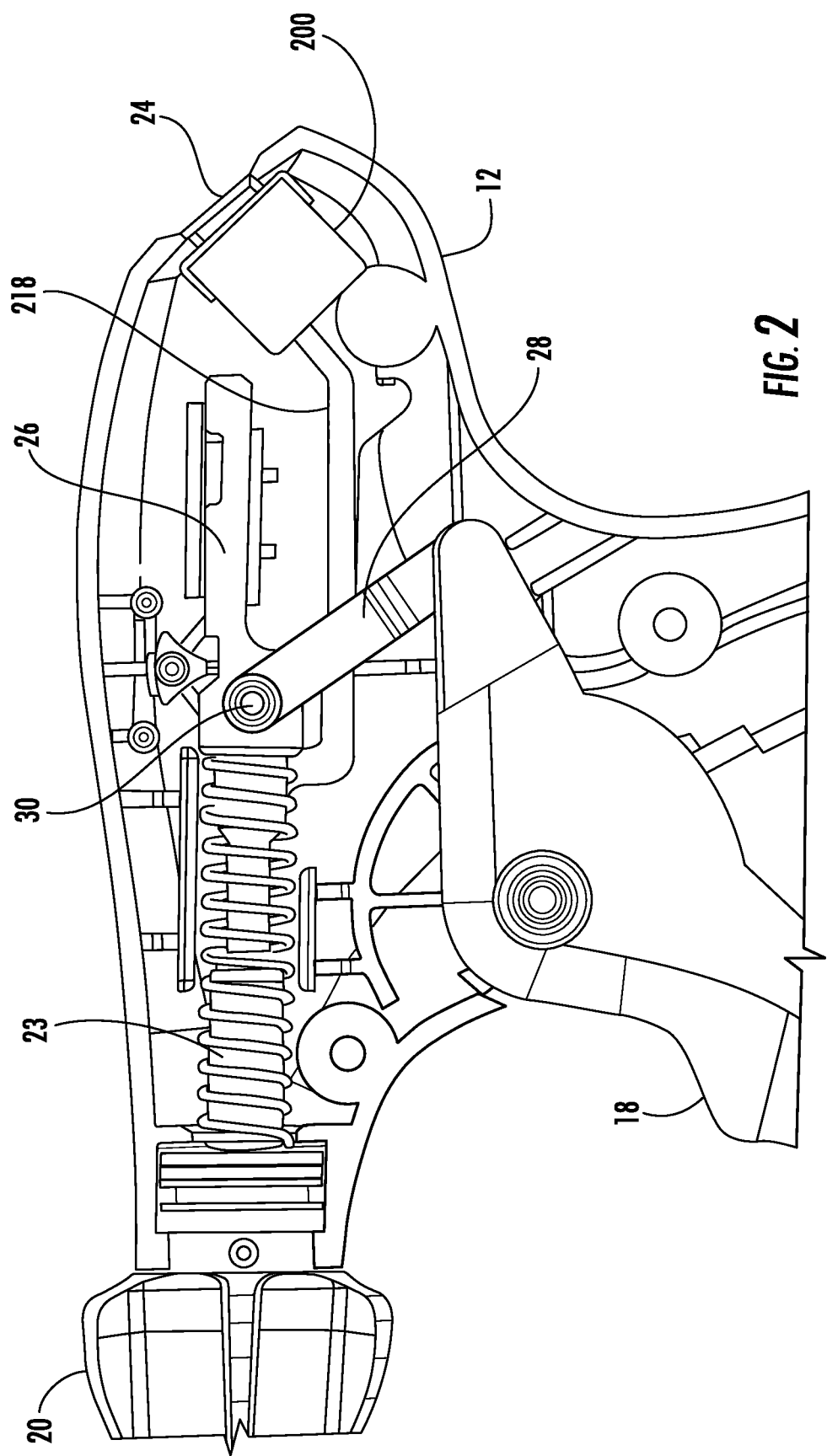
FIG. 2 is a side view, with a half of a body removed, of a handle assembly of the surgical clip applier including a counter assembly.

Referring now to FIGS. 1A, 1B, and 2, surgical clip applier 10 generally includes a handle assembly 12 and an elongated member 14 extending distally from handle assembly 12. Handle assembly 12 may be formed of a plastic material while elongated tubular member 14 may be tubular and formed of stainless steel or any other metal material. A pair of jaws 16 is mounted on a distal end of elongated tubular member 14 and is actuated by a trigger 18 movably mounted in handle assembly 12. The pair of jaws 16 defines a channel 22 for receipt of a surgical clip "C" therein. The pair of jaws 16 may be formed of stainless steel or titanium. A knob 20 is rotatably mounted on a distal end of handle assembly 12 and affixed to elongated tubular member 14 to provide 360 degree rotation of elongated tubular member 14 and the pair of jaws 16 about its longitudinal axis. A counter window 24 is provided in handle assembly 12 to view an indicator, such as, for example, a counter assembly associated with handle assembly 12. Handle assembly 12 includes a longitudinally movable rack bar 26 (FIG. 2) which is connected to trigger 18 by means of a wishbone link 28 (FIG. 2). A pin 30 is provided to connect wishbone link 28 to rack bar 26 (FIG. 2). Rack bar 26 is provided for advancing and crimping a surgical clip between jaws 16 in response to actuation of trigger 18. Rack bar 26 is biased to a proximal position by a return spring 23 (FIG. 2). A complete description of the inner-workings and operation of surgical clip applier can be found in commonly-assigned U.S. Pat. No. 7,905,890 entitled "ENDOSCOPIC SURGI-CAL CLIP APPLIER" to Whitfield et al., the entire content of which is hereby incorporated by reference herein.

Moving now to FIGS. 3A-3C, 4A, 4B, and 5A-5E a counter assembly 200, for use in surgical clip applier 10, is illustrated. Counter assembly 200 is configured to provide an indication of either the number of clips fired or the number of clips remaining within surgical clip applier 10. Counter assembly 200 includes a housing 202, an actuator 240, a driver 230, a pin assembly 224, and a counting mechanism 250.

Housing 202 of counter assembly 200 includes a first housing half 202a and a second housing half 202b. First and second housing halves 202a, 202b may be snap fitted together or connected in any other appropriate method. When connected, first and second housing halves 202a, 202b define a window 220 therein which coincides with counter window 24 of handle assembly 12. Additionally, housing 202 encases the other components of counter assembly 200.

First housing half 202a of housing 202 defines and/or includes a circular recess 204, a stationary post 206 including a plurality of locking teeth 208, a linear channel 210, a vertical slot 212, a pin aperture 214, a driver slot 216, and an actuator slot 218.

Circular recess 204 is configured and adapted to rotationally support counting mechanism 250. A circumference of circular recess 204 is larger than an outer circumference of counting mechanism 250. Circular recess 204 is configured to align the counting mechanism 250 within first housing half 202a and to ensure that the plurality of locking teeth 208 of stationary post 206 remain engage with a plurality of fingers 264 of a locking spring assembly 260 of counting mechanism 250.

Stationary post 206 is concentrically positioned in circular recess 204 of first housing half 202a and extends perpendicular therefrom. An outer circumference of stationary post 206 includes a plurality of locking teeth 208, which allows the counting mechanism 250 to only transition/rotate in one direction upon engagement of driver 230 therewith.

Figure 3A:
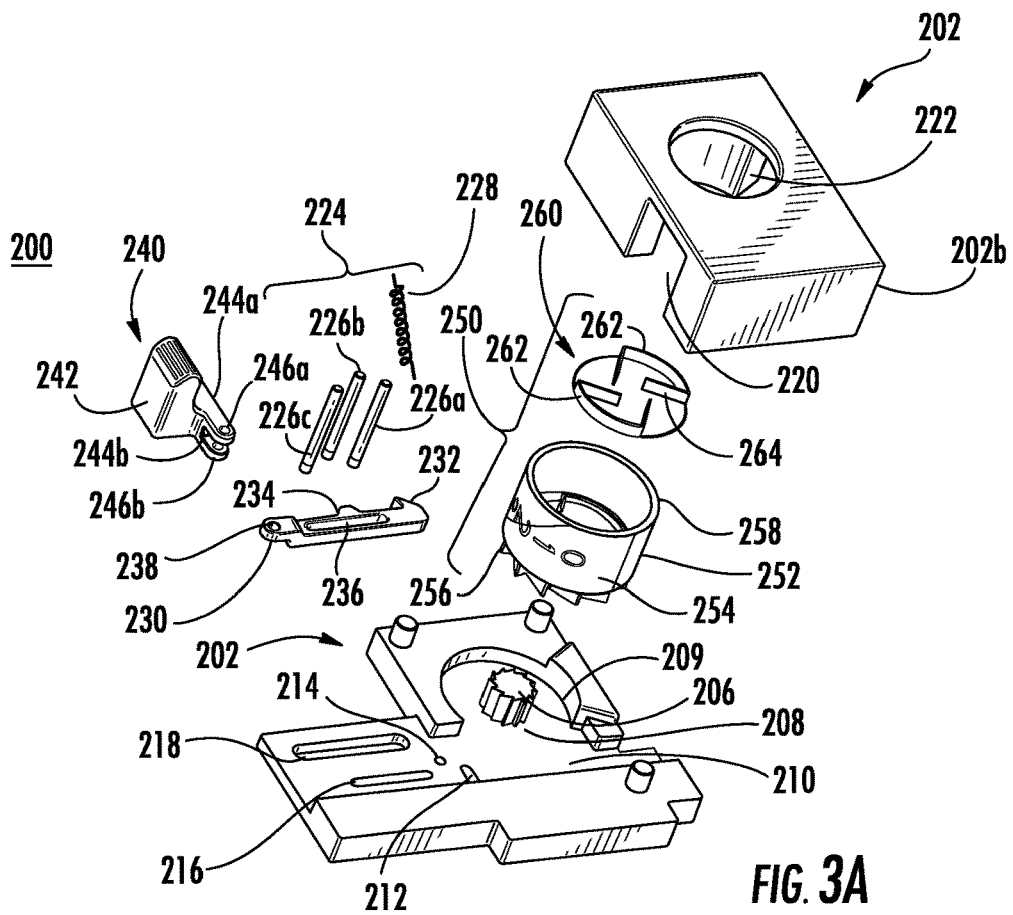
FIG. 3A-3C are enlarged views of a counter assembly of the surgical clip applier of FIG. 1A.

Linear channel 210 is configured to receive driver 230, and permits linear translation thereof, for example, a horizontal translation between an initial position and a final position. Linear channel 210 is positioned in relation to circular recess 204 to permit interaction between a plurality of actuation features 256 of a counting wheel 252 of counting mechanism 250 and a grasping protrusion 232 of driver 230. In one embodiment, linear channel 210 is defined below circular recess 204 (FIG. 3A). In another embodiment, linear channel 210 is defined above circular recess 204 (not illustrated).

Vertical slot 212 is configured to receive a vertical translating pin 226a of pin assembly 224, and permits vertical translation thereof. Vertical slot 212 is defined within linear channel and positioned proximate to circular recess 204. Pin aperture 214 is configured to receive a stationary pin 226b of pin assembly 224. Pin aperture 214 is positioned proximately to vertical slot 212. Driver slot 216 is configured to receive a horizontal translating pin 226c, and permits linear translation of driver 230, such as a horizontal translation of horizontal translating pin 226c between an initial position and a final position. Drive slot 216 extends away from pin aperture 214 and is positioned proximately thereto. Actuator slot 218 is configured to receive actuator 240, and permits linear translation of actuator 240, such as a horizontal translation of actuator 240 between an initial position and a final position. Actuator slot 218 is defined parallel to driver slot 216. The length of both driver slot 216 and actuator slot 218 allow for a full stroke of surgical clip applier 10.

Second housing half 202b of housing 202 defines an aperture 222 therein that is adapted and configured to fit counting mechanism 250, thereby facilitating a connection of all of the components of counter assembly 200 (FIG. 3A).

Counting mechanism 250 includes a counting wheel 252 and a locking spring assembly 260. In some embodiments, counting wheel 252 is formed into a hollow cylinder. Counting wheel 252 includes indicia 254 positioned or displayed circumferentially thereabout (FIG. 3A). Indicia 254 may take the form of digits, which indicate either the number of remaining surgical clips or the number of surgical clips that have been fired. Indicia 254 may take other forms, such as one or more colors to indicate the number of surgical clips remaining. For example, the color red may indicate that a small number of surgical clips remain. Additionally, indicia 254 may include a combination of different indicia, such as alpha-numeric digits and colors. For example, as a number of indicia 254 of counting wheel 252 increases or decreases, a color of indicia 254 of counting wheel 252 may also change.

Counting wheel 252 includes a plurality of actuation features 256, which may be positioned circumferentially thereabout. In some embodiments, the plurality of actuation features 256 take the form of teeth, which allow counting wheel 252 to only transition/rotate in one direction upon engagement with driver 230. Additionally, the number of actuation features 256 may be equivalent to the number of surgical clips of clip applier 10.

Figure 3B:
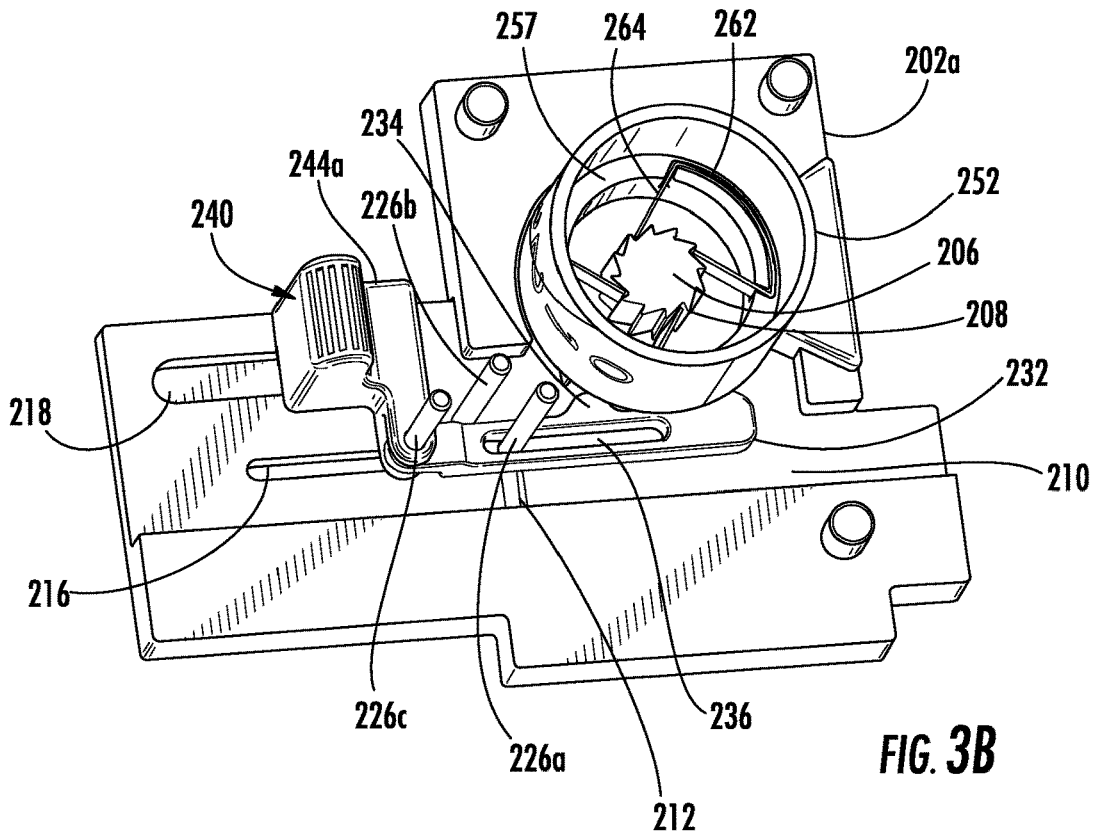
Figure 3C:
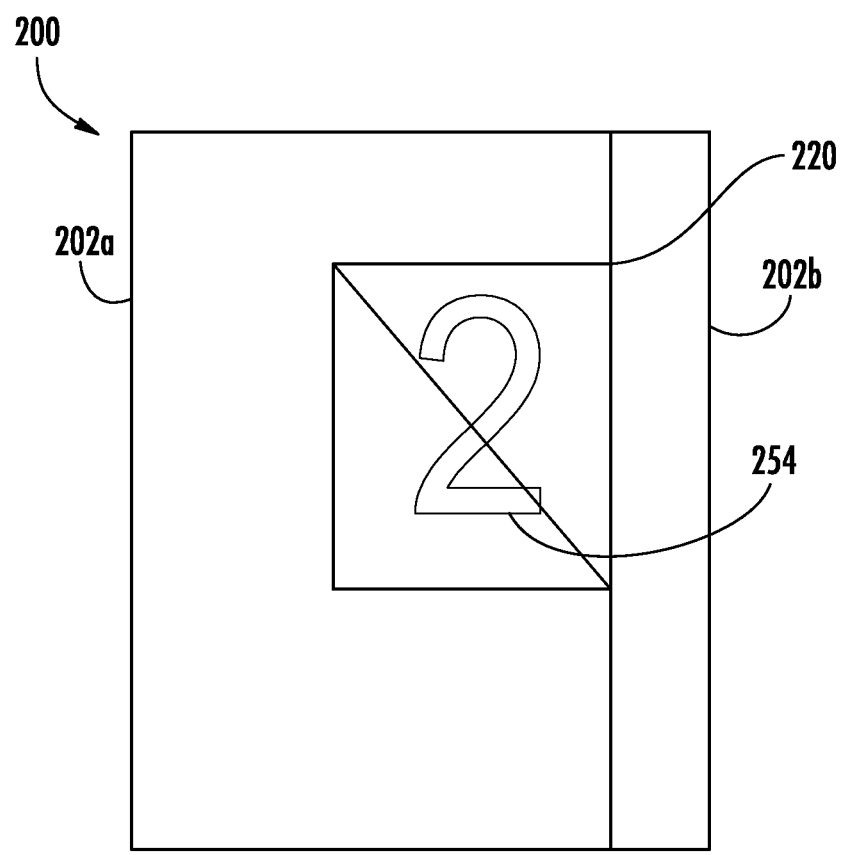

In some embodiments, the counting wheel 252 includes an inner circular shelf 257 (FIG. 3B). Inner circular shelf 257 is adhered to an inner surface of counting wheel 252 and/or formed with counting wheel 252. Inner circular shelf 257 extends radially from the inner surface of counting wheel 252. In one embodiment, inner circular shelf 257 is continuous and extends the entire inner surface of counting wheel 252 (FIG. 3B). In other embodiments, inner circular shelf 257 is non-continuous and extends the entire inner surface of counting wheel 252 (not illustrated). In this embodiment, inner circular shelf 257 includes multiple pieces separated by spaces. Inner circular shelf 257 is configured to provide a surface for a locking spring assembly 260.

Figure 4A:
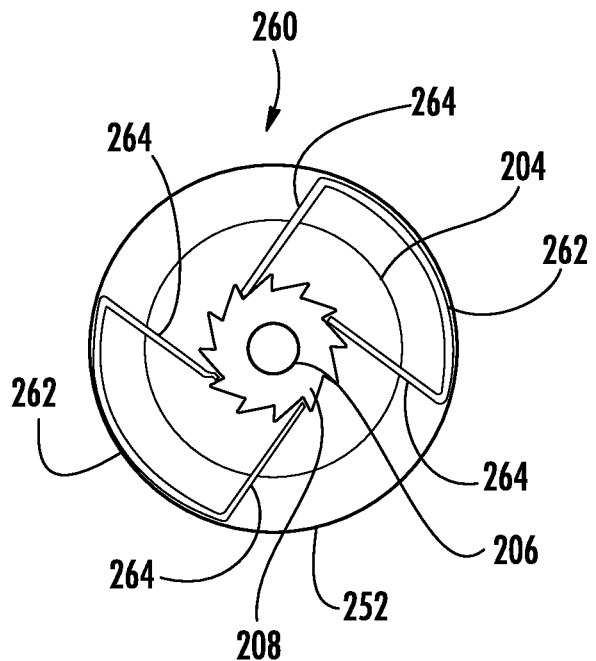
FIGS. 4A and 4B are enlarged views of embodiments of locking spring assembly of the counter assembly of FIG. 3A.
Figure 4B:
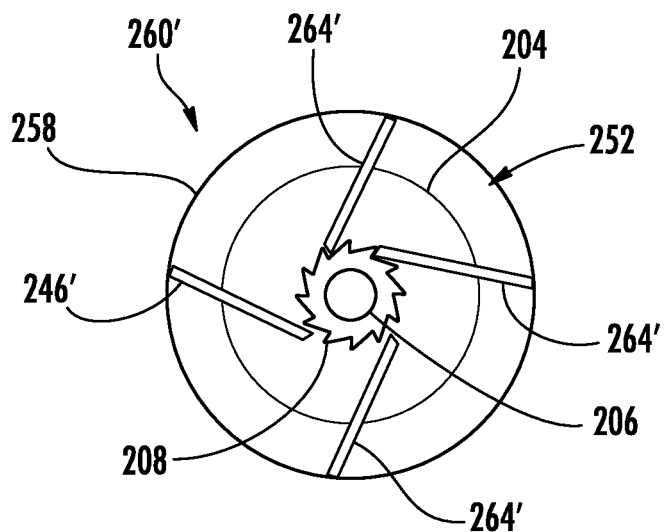

As seen specifically in FIGS. 3A, 4A, and 4B, embodiments of locking spring assemblies are displayed. As seen in FIG. 4A, one embodiment of locking spring assembly 260 includes a plurality of bodies 262 and a plurality of fingers 264. In some embodiments, each body 262 of the locking spring assembly 260 is press fitted to an inner surface 258 of counting wheel 252. In other embodiments, each body 262 of the locking spring assembly 260 is adhered and/or fused to inner circular shelf 257 of counting wheel 252. The plurality of fingers 264 extend from the plurality of bodies 262. In one embodiment, two fingers 264 will extend from each body 262. In this embodiment, body 262 and the two fingers 264 form a generally "C" shape, such that one finger extends almost perpendicularly from body 262 and the other finger extends almost parallel from body 262. Fingers 264 are substantially orthogonal to one another, such that the two fingers are spaced 90 degrees apart. In other embodiments, each finger 264 takes the form of a long protrusion which is positioned at an angle with respect to the body 262 that the finger 264 extends therefrom. Each finger 264 is resilient and flexible, and extends in a substantially tangential direction to an inner surface 258 of counting wheel 252.

The angle and size of each finger 264 is compatible with a profile of each locking tooth 208 of stationary post 206 of first housing half 202a, such that the angle of each finger 264 allows counting wheel 252 to transition/rotate in a first direction, but prohibits counting wheel 252 to transition/rotate in a second direct, opposite the first direction.

FIG. 4B illustrates another embodiment of a locking spring assembly in accordance with the present disclosure, and is generally designated by 260'. In this embodiment, locking spring assembly 260' includes a plurality of fingers 264'. The fingers 264' extend from the inner surface 258 of the counting wheel 252. In one embodiment, fingers 264' are integrally formed with inner surface 258 of counting wheel 252. In other embodiments, fingers 264' are adhered to or fused to inner circular shelf 257 (not illustrated) of counting wheel 252 by any appropriate method. Generally, each finger 264' is substantially orthogonal to one another, such that the fingers 264' are spaced 90 degrees apart. Additionally, each finger 264' may take the form of a protrusion which is positioned at an angle with respect to inner surface 258 of counting wheel 252. Specifically, each finger 264' is resilient and flexible, and extends in a substantially tangential direction to inner surface 258 of counting wheel 252. Each finger 264' extends in a generally common tangential direction as the plurality of actuation features 256. The angle and size of each inner finger 264' is compatible with a profile of each locking tooth 206 of stationary post 206 of first housing half 202a, such that the positioning angle of each finger 264' allows counting wheel 252 to transition/rotate in a first direction, but prohibits counting wheel 252 to transition/rotate in a second direct, opposite the first direction.

In operation, during rotation of counting wheel 252 in the first direction, each finger 264 flexes over the plurality of locking teeth 208 of stationary post 206 thereby allowing the counting wheel 252 to transition/rotate in reaction to driver 230 and actuator 240. After fingers 262 flex over the plurality of locking teeth 208, each finger 262 is positioned within the valleys defined between the plurality of locking teeth 208 of stationary post 206 thereby prohibiting movement of counting wheel 252 in a second direction, upon the return of driver 230 and actuator 240.

Referring back to FIG. 3A, driver 230 includes a grasping protrusion 232, a positioning protrusion 234, a channel or window 236, and an aperture 238. Grasping protrusion 232 extends and/or is formed at a proximal end of the driver 230. Grasping protrusion 232 is configured to engage the plurality of actuation features 256 of counting wheel 252. Positioning protrusion 234 extends from and/or is formed upon an upper surface of driver 230. The position of positioning protrusion 234 facilitates engagement of driver 230 with pin assembly 224. Channel or window 236 is defined through driver 230 and extends between the proximal end and a distal end of driver 230. Channel 236 is configured to receive vertical translating pin 226a of pin assembly 224. Aperture 238 is defined through the distal end of driver 230. Aperture 238 is configured to receive horizontal translating pin 226c of pin assembly 224.

With continue reference to FIG. 3A, as briefly mentioned above, pin assembly 224 includes a vertical translating pin 226a, a stationary pin 226b, a horizontal translating pin 226c, and a spring 228. Also as described above, vertical translating pin 226a is configured to be received within channel 236 of driver 230. Vertical translating pin 226a is configured to linearly/vertically translate within vertical slot 212 between a first position and a second position. Spring 228 is connected to vertical translating pin 226a and is configured to bias vertical translating pin 226a to the first position. In the first position, vertical translating pin 226a is horizontally aligned with horizontal translating pin 226c, while in the second position, vertical translating pin 226a is horizontally misaligned with horizontal translating pin 226c. Stationary pin 226b is configured to engage with positioning protrusion 234 of driver 230. Horizontal translating pin 226c is positioned at the distal end of driver 230 and attaches driver 230 to first housing half 202a. Also, horizontal translating pin 226c is configured to linearly/horizontally translate within driver slot 216 between a first position and a second position. In the first position, horizontal translating pin 226c is positioned proximal of stationary pin 226b and vertical translating pin 226a, while in the second position, horizontal translating pin 226c is positioned distal to stationary pin 226b and vertical translating pin 226a. Additionally, horizontal translating pin 226c is configured to allow driver 230 to pivot in response to engagement with stationary pin 226b.

With reference to FIGS. 3A and 3B, actuator 240 includes a body 242, a pair of arms 244a, 244b, which each define an aperture 246a, 246b, respectively. Actuator 240 is coupled to rack bar 26 and configured to translate in reaction to actuation of the surgical clip applier 10. Body 242 of actuator 240 is coupled to first housing half 202a and is configured to linearly/horizontally translate within actuator slot 218. Actuator 240 includes arms 244a, 244b that extend from body 242. Apertures 246a, 246b are defined through arms 244a, 244b, respectively, and are configured to receive horizontal translating pin 226c of pin assembly 224, thus connecting actuator 240 to driver 230.

Referring back to FIG. 3B, a method of assembly of counter assembly 200 is illustrated. Actuator 240 is coupled to the first housing half 202a via actuator slot 218. Driver 230 is coupled to actuator 240 via horizontal translating pin 226c of pin assembly 224. Driver 230 is seated within linear channel 210 of first housing half 202a with vertical translating pin 226a positioned within channel 236 of driver 230 and vertical slot 212, and horizontal pin 226b positioned within aperture 238 of driver 230 and the apertures 246a, 246b of actuator 240. Stationary pin 226b is positioned within pin aperture 214. Spring 228 is coupled to vertical translating pin 226a of pin assembly 224. Locking spring assembly 260 is fitted within counting wheel 252. Counting wheel 252 is seated within circular recess 204 of first housing half 202a with stationary post 206 extending therethrough. The plurality of locking teeth 208 of stationary post 206 engaging with the plurality of fingers 262 of locking spring assembly 260. Counting assembly 250 is seated within aperture 222 of second housing half 202b. First housing half 202a and second housing half 202b are snap-fitted together thereby assembling all components of counter assembly 200.

In an alternative embodiment, counter assembly 200 may not include housing 202. In this embodiment, the other components of counter assembly 200 will be directly coupled to or formed in handle assembly 12 of surgical clip applier 10, such that first circular recess 204, stationary post 206 including the plurality of locking teeth 208, linear channel 210, vertical slot 212, pin aperture 214, driver slot 216, and actuator slot 218 will be formed and defined within a first half of handle assembly 12 (not illustrated). A second circular recess (not illustrated), configured to receive the counting wheel 252 and permit rotation thereof, will be defined within a second half of handle assembly 12 (not illustrated). In this embodiment, each component engages with one another similarly or exactly how they engage with one another as described above.

Figure 5A:
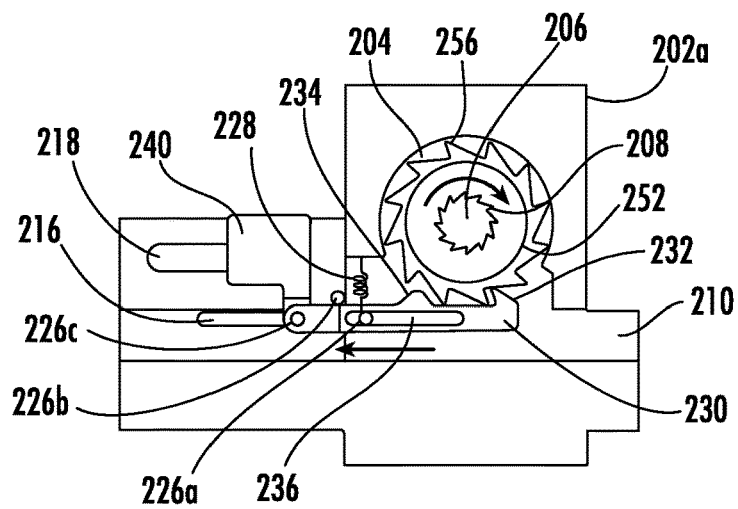
FIGS. 5A-5E are enlarged views of components of the counter assembly of FIG. 3A.
Figure 5B:
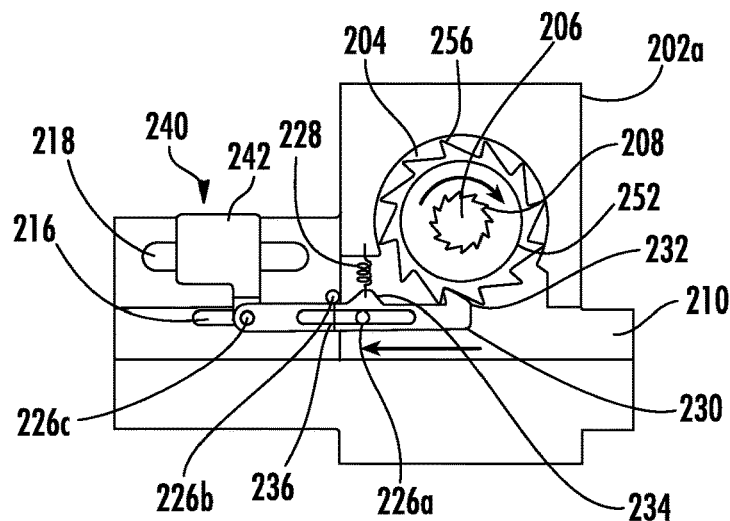

Referring now to FIGS. 5A-5E, actuation of counter assembly 200 is illustrated. In FIG. 5A, driver 230, vertical translating pin 226a, horizontal translating pin 226c, and actuator 240 are all in a first position. As surgical clip applier 10 is actuated via trigger 18 (FIG. 1A), actuator 240 begins to transition or translate distally from the first position to a second position. Driver 230 is coupled to actuator 240 via horizontal translating pin 226c, and thus, driver 230 and horizontal translating pin 226c also begin to transition or translate from the first position to a second position.

Figure 5C:
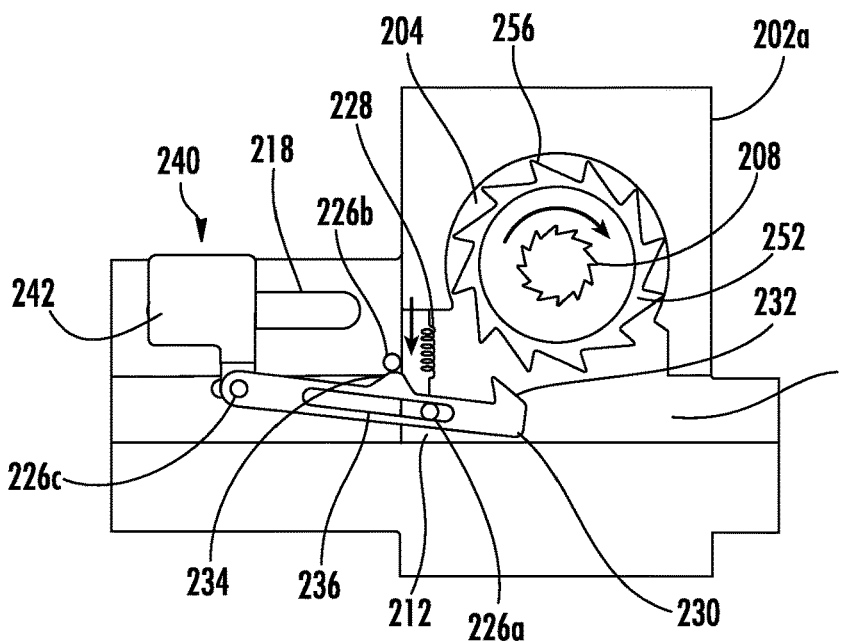
Figure 5D:
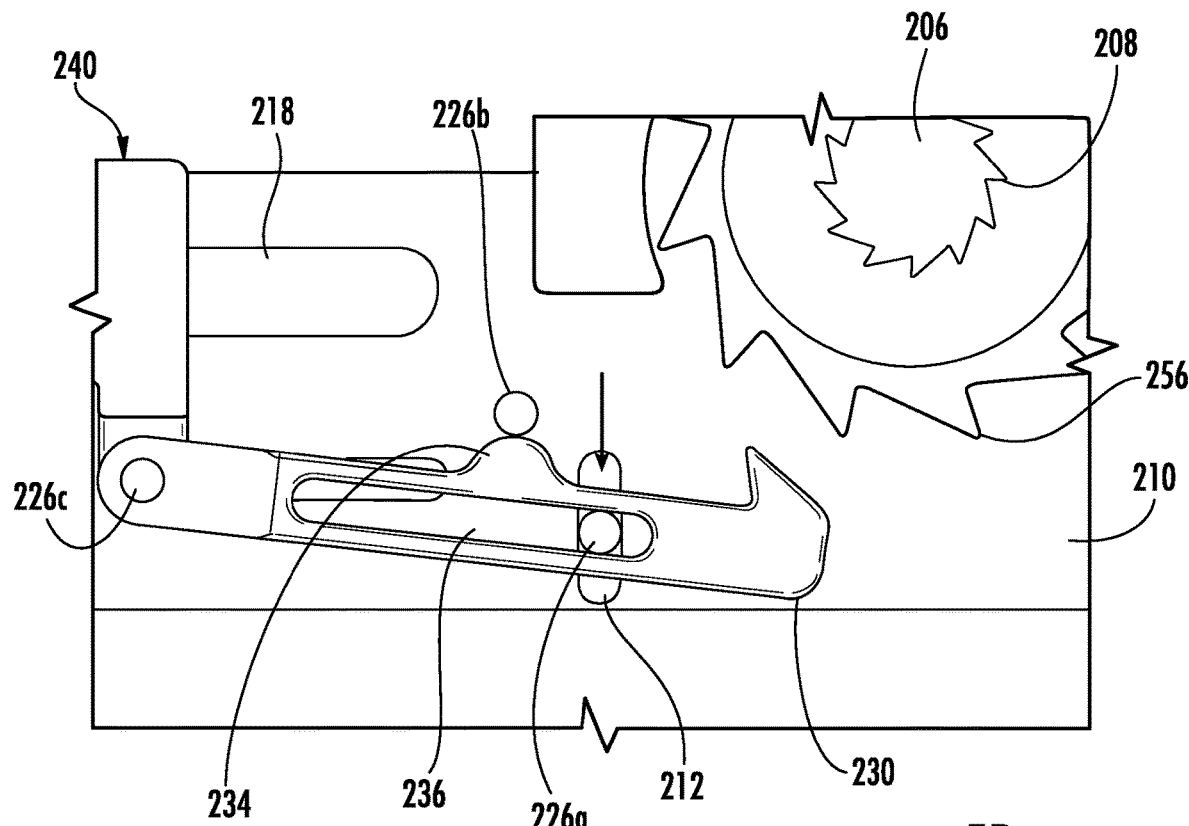
Figure 5E:
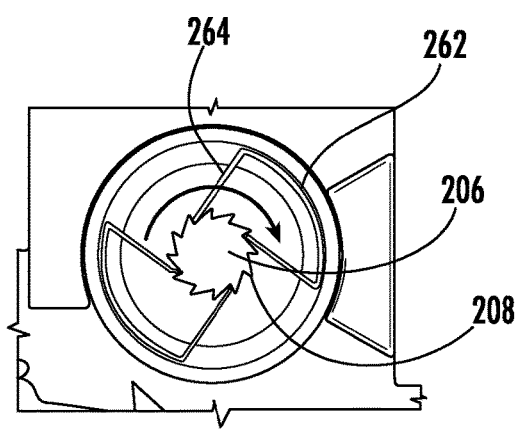

As driver 230 is translated, grasping protrusion 232 of driver 230 engages with at least one of the plurality of actuation features 256 of counting wheel 252 thereby causing the counting wheel 252 to rotate in a first direction. The engagement between grasping protrusion 232 of driver 230 and the actuation feature 256 of counting wheel 252 remains until positioning protrusion 234 of driver 230 engages with stationary pin 226b of pin assembly 224 (FIG. 5C). As driver 230 continues to translate distally, upon engagement of positioning protrusion 234 with stationary pin 226b, driver 230 transitions or translates vertical translating pin 226a between the first position and a second position whereby grasping protrusion 232 of driver 230 pivots and disengages from the plurality of actuation features 256 of counting wheel 252. In some embodiments, upon engagement between the grasping protrusion 232 of driver 230 and the plurality of actuation features 256, counting wheel 252 will begin to rotate from an initial position. Counting wheel 252 will rotate 30 degrees from the initial position before positioning protrusion 234 of driver 230 engages with stationary pin 226b. As counting wheel 252 continues to rotate past 30 degrees from the initial position, positioning protrusion 234 will engage with stationary pin 226b causing the driver 230 to cam down and disengage with the plurality of actuation features of counting wheel 252.

Driver 230 and actuator 240 continue to linearly/horizontally translate until reaching the second position, wherein the trigger 18 is full compressed and surgical clip applier 10 is fully actuated. In the second position, the positioning protrusion 234 of driver 230 is distal to stationary pin 226b. Upon release of trigger 18, driver 230 and actuator 240 begin to translate proximally from the second position back to the first position. Again, positioning protrusion 234 of driver 230 engages with stationary pin 226b thereby forcing driver 230 to pivot. Simultaneously, vertical translating pin 226a translates from the first position to the second position. Once positioning protrusion 234 is proximal to stationary pin 226b, driver 230 is again engaged with the plurality of actuation features 256 of the counting wheel 252.

Locking spring assembly 260 permits rotation of counting wheel 252 in the first direction. In operation, during rotation of the counting wheel 252, in the first direction, the plurality of fingers 264 flex radially outward upon engagement with the plurality of locking teeth 208 of the stationary post 206. In contrast, free ends of the plurality of fingers 264 of locking spring assembly 260 abut the plurality of locking teeth 208 of stationary post 206, if counting wheel 252 should begin to rotate in the second direction, thus prohibiting rotation of counting wheel 252 in a second direction. The shape and positioning of the plurality of fingers 264 prevents counting wheel 252 from rotating in a second direction.

As described above, counting wheel 252 is configured for unidirectional rotation. The cooperation of the plurality of fingers 264 of locking spring assembly 260 and the plurality of locking teeth 208 of stationary post 206 prohibits rotation of counting mechanism 250 during the translation of driver 230 and actuator 240 from the second/distal position to the first/proximal position, for example, a secondary direction opposite to the first direction.

Referring back to FIG. 2, as noted above, handle assembly 12 is provided with a counter window 24 at a proximal end thereof which may reveal counter assembly 200 associated therewith. Window 220 of counter assembly 200 aligns with counter window 24 such that user may view indicia 254 during use of clip applier 10. As mentioned above, driver 230 causes the rotation of counter assembly 250 by using the linear force created by the transition of the rack bar 26, actuator 240, and driver 230.

It should be understood that the forgoing description is only illustrative of the present clip applier and counter assembly. Various alternatives and modifications can be devised by those skilled in the art without departing from the disclosure. Accordingly, the present disclosure is intended to embrace all such alternatives, modifications, and variances. The embodiments described with reference to the attached drawings are presented only to demonstrate certain examples of the clip applier and counter assembly. Other elements, steps, methods, and techniques that are insubstantially different from those described above and/or in the appended claims are also intended to be within the scope of the disclosure.

What is claimed is:

1. A surgical clip applier, comprising:
   a handle assembly;
   an elongated tubular member extending distally from the handle assembly;
   a rack bar translatably supported in the handle assembly; and
   a counter assembly supported in the handle assembly, the counter assembly including:
      a housing having a first housing half and a second housing half;
      a stationary post positioned within the first housing half and including a plurality of locking teeth;
      a counting wheel positioned to rotate within the housing, the counting wheel including indicia visible through the handle assembly;
      a plurality of actuation features positioned circumferentially about the counting wheel;
      a locking spring assembly including a plurality of fingers, the locking spring assembly positioned within the counting wheel and configured to engage the plurality of locking teeth of the stationary post, wherein the engagement of the plurality of fingers of the locking spring assembly and the plurality of locking teeth of the stationary post prohibits multidirectional rotation of the counting wheel;
      a driver coupled to the rack bar for translation therewith, the driver including a grasping protrusion and a positioning protrusion, the driver positioned to translate between a proximal position and a distal position, wherein transitioning from the proximal position to the distal position, the grasping protrusion of the driver engages an actuation feature of the plurality of actuation features to rotate the counting wheel to change the indicia of the counting wheel visible through the handle assembly; and
      a pin assembly including a stationary pin configured to engage with the positioning protrusion of the driver, wherein during transitioning of the driver from the proximal position to the distal position, the positioning protrusion of the driver engages the stationary pin to pivot the driver, whereby the driver disengages from the plurality of actuation features of the counting wheel.

2. The surgical clip applier of claim 1, wherein the pin assembly further includes a vertical translating pin, a horizontal translating pin, and a spring, wherein each of the vertical translating pin, the horizontal translating pin, and the spring is configured to permit the engagement and the disengagement between the stationary pin of the pin assembly and the positioning protrusion of the driver.

3. The surgical clip applier of claim 2, wherein the spring is connected to the vertical translating pin thereby allowing the vertical translating pin to transition between a first position and a second position.

4. The surgical clip applier of claim 3, wherein the driver defines a channel configured to receive the vertical translating pin of the pin assembly thereby connecting the driver to the pin assembly.

5. The surgical clip applier of claim 4, wherein the vertical translating pin is positioned within a vertical slot defined in at least one of the first housing half and second housing half and wherein the vertical translating pin is biased to the first position by the spring, the vertical translating pin being configured to translate from the first position to the second position in response to the driver engaging with the positioning protrusion.

6. The surgical clip applier of claim 5, further including an actuator coupled to the rack bar and the driver.

7. The surgical clip applier of claim 6, wherein the horizontal translating pin couples the driver to the actuator, wherein the horizontal translating pin translates in response to a translation of the actuator and thereby causes the driver to translate.

8. The surgical clip applier of claim 7, wherein the actuator is positioned within an actuator slot defined in at least one of the first housing half or the second housing half, the actuator translates in response to the translation of the rack bar and the driver translates in reaction to the translation of the actuator.

9. The surgical clip applier of claim 1, wherein the first housing half defines a linear channel configured to receive the driver.

10. The surgical clip applier of claim 1, wherein each finger of the plurality of fingers of the locking spring assembly is resilient and flexible, and extends in a substantially tangential direction to an inner surface of the counting wheel.

11. The surgical clip applier of claim 10, wherein the substantially tangential orientation and the length of each finger of the plurality of fingers prohibits multidirectional rotation of the counting wheel.

12. The surgical clip applier of claim 1, wherein the locking spring assembly includes a plurality of bodies and the plurality of fingers, wherein the plurality of fingers extend from the plurality of bodies.

13. The surgical clip applier of claim 1, wherein the housing further defines a circular recess configured to receive the counting wheel.

14. The surgical clip applier of claim 13, wherein the stationary post is concentrically positioned within the first housing half in relation to the circular recess.

15. The surgical clip applier of claim 1, wherein the second housing half defines an aperture configured to receive the counting wheel.

16. The surgical clip applier of claim 1, further including a plurality of surgical clips disposed within the elongated tubular member, wherein the indicia of the counting wheel indicates a remaining number of the plurality of surgical clips.

17. The surgical clip applier of claim 16, wherein a number of actuation features of the plurality of actuation features is equal to an initial number of surgical clips of the plurality of surgical clips.

18. The surgical clip applier of claim 16, wherein the indicia includes a plurality of numbers to indicate the remaining number of surgical clips of the plurality of surgical clips.

19. The surgical clip applier of claim 16, wherein the indicia includes one or more colors to indicate the remaining number of surgical clips of the plurality of surgical clips.

\* \* \* \* \*